United States Patent
Wittig et al.

(10) Patent No.: US 9,212,366 B2
(45) Date of Patent: Dec. 15, 2015

(54) IMMUNE MODULATING OLIGONUCLEOTIDES IN CONNECTION WITH CHEMOTHERAPEUTIC MEASURES

(75) Inventors: Burghardt Wittig, Berlin (DE); Manuel Schmidt, Berlin (DE); Heribert Bohlen, Cologne (DE)

(73) Assignee: Mologen AG, Berline (DE)

( * ) Notice: Subject to any disclaimer, the term of this patent is extended or adjusted under 35 U.S.C. 154(b) by 1115 days.

(21) Appl. No.: 11/573,529

(22) PCT Filed: Aug. 9, 2005

(86) PCT No.: PCT/EP2005/008770
§ 371 (c)(1),
(2), (4) Date: Oct. 31, 2008

(87) PCT Pub. No.: WO2006/021347
PCT Pub. Date: Mar. 2, 2006

(65) Prior Publication Data
US 2009/0053250 A1      Feb. 26, 2009

(30) Foreign Application Priority Data
Aug. 9, 2004   (WO) ............... PCT/DE2004/001801

(51) Int. Cl.
A61K 31/711 (2006.01)
C12N 15/117 (2010.01)
A61K 39/00 (2006.01)

(52) U.S. Cl.
CPC ..... *C12N 15/117* (2013.01); *A61K 2039/55561* (2013.01); *C12N 2310/17* (2013.01); *C12N 2310/53* (2013.01)

(58) Field of Classification Search
None
See application file for complete search history.

(56) References Cited

U.S. PATENT DOCUMENTS

| 6,653,292 B1 | 11/2003 | Weiher et al. |
| 6,849,725 B2 | 2/2005 | Junghans et al. |
| 2003/0125279 A1 * | 7/2003 | Junghans et al. ............... 514/44 |

FOREIGN PATENT DOCUMENTS

| WO | WO98/06416 | * | 2/1998 |
| WO | 01/07055 A1 | | 2/2001 |
| WO | 02/60476 A2 | | 8/2002 |
| WO | 2006/015872 | | 2/2006 |

OTHER PUBLICATIONS

Drug Facts and Comparisons@ (1999 Edition, pp. 3285-3300).*
Hagner et al (Molecular Therapy, May 2004, vol. 9, suppl. 1, pp. S244-S245).*
Milas et al (Cancer Research, Aug. 1, 2004, vol. 64, pp. 5074-5077).*
Weigel et al (Clinical Cancer Research, 2003, vol. 9, pp. 3105-3114).*
Stillwell et al (Cancer, 1988, vol. 61, pp. 451-457).*
"Mologen's dSLIM Technology Evaluated in Clinical Phase 2 Study Against Colorectal Carcinoma," Mologen, online released Jul. 3, 2003, available at http://www.thefreelibrary.com/Mologen's dSLIM Technology Evaluated in Clinical Phase 2 Study . . . -a0131702574, retrieved Aug. 20, 2010.

* cited by examiner

*Primary Examiner* — Karen Canella
(74) *Attorney, Agent, or Firm* — 24IP Law Group; Timothy R DeWitt; Shelly Cermac (57) ABSTRACT

The invention relates to the use of immune modulators on the basis of DNA in the form of covalently closed nucleic acid molecules comprising immune stimulatory sequence motifs, for the production of a pharmaceutical for the therapeutic treatment of tumor diseases in combination with chemotherapeutic drugs.

8 Claims, 7 Drawing Sheets

IMMUNE MODULATING OLIGONUCLEOTIDES IN CONNECTION WITH CHEMOTHERAPEUTIC MEASURES

This is the U.S. national stage of International application PCT/EP2005/008770, filed Aug. 9, 2005 designating the United States.

DESCRIPTION

The invention relates to the use of a covalently closed nucleic acid molecule for the production of a pharmaceutical, which serves the purpose of therapeutic treatment of tumor diseases in combination with chemotherapeutic drugs.

Tumor diseases are one of the most significant causes of mortality in the industrialized world. Established methods of therapy such as surgical removal, radiation and chemotherapy often lead only to a regression of the disease for a limited amount of time. Certain carcinogenic diseases such as non-small cell bronchial carcinoma cannot be operated on, and the life expectancy of patients is about one year after diagnosis, with or without therapy.

The efficacy of chemotherapy mainly relies on the fact that cells that divide and multiply continuously are sensitive to the treatment with cytotoxic pharmaceuticals. These cells are mainly malign tumor cells. Since healthy cells of different organs are dividing as well, these also react sensitively to chemotherapy. Some cytostatic drugs prooke cancer themselves, are mutagenic or damaging to the germline. For this reason, a short duration of therapy with only few cycles of chemo therapy would be of great advantage for the patients in order to reduce the side effects that the patients experiences.

One of the great challenges in the application of chemotherapy is not only the reduction of side effects. It has also been shown that some cancers develop a certain resistance against the pharmaceuticals employed in chemotherapy. In spite of all, sometimes significant, side effects, chemotherapy will remain one of the pillars of treatment of neoplastic diseases.

STATE OF THE ART

Chemotherapy based treatments usually are performed in several cycles, interrupted by breaks of 2 to 4 weeks. During this time, the patient can recover from the side effects.

Chemotherapeutic drugs destroy tumor cells by biochemical reactions that initiate cell death.

Cells can perish by two different ways of cell death: by apoptosis, programmed cell death, or by necrosis, actively induced cell death. Tumor cells die by necrosis. The cell's nucleus decays and the internal structures of the tumor cell dissolve. This provokes an immune response, as a consequence of which, cells of the immune system are attracted. They define the border to the adjacent viable tissue and actively decay the proteins of the necrotic cells.

In contrast to pathogens that enter the body, the tumor-associated antigens (TAA) that are liberated during that decay only induce a weak immune response. In order to induce a sufficient immune response against such antigens, the existing threshold of immune tolerance must be overcome. For this reason, one approach to therapy relies on increasing the effect of chemotherapy by combining it with other therapies, e.g. additional applications of interferons or cytokines, in order to support the patient's immune system (McDermott et al., 2004, Expert Opin Biol Ther. 4: 455-68).

In experiments relating to the stimulation of immune responses, it has been observed that certain nucleic acid sequences that contain CpG motives (CpG: unmethylated cytosin-guanosine) can have an enormous immune stimulatory effect. Such non-methylated CpG motifs occur in bacterial DNA and represent a danger signal for the immune system (Krieg, Nat. Med 2003, 9: 831-835).

In mouse experiments it was shown that the application of CpG-rich DNA sequences leads to a strong activation of B-lymphocytes and stimulates the expression of certain cytokines, for example IL-6 and GM-CSF. In addition, CpG motifs induce a cytotoxic, Th1-biased, immune response by means of the cytokines interleukin 12, interferon gamma and tumor necrosis factor. Cytotoxic lymphocytes of the Th1 arm are able to attack and destroy tumor cells. In addition, CpG motifs lead to the activation of NK (natural killer) cells and dendritic cells (Klinman et al., 1996, PNAS USA 93: 2879, Sparwasser et al., 1998, Eur. J. Immunol. 28: 2045).

Clinical trials in phase III are conducted relating to the use of CpG-containing oligonucleotides in order to support the therapy of metastasised mama carcinoma with Herceptin (HER). This therapy led to a regression of tumor in a significant fraction of the patients (Baselga et al., 1996, J. Clin. Oncol. 14: 737-744). In contrast to chemotherapy, the underlying principle of Herceptin action is very different. In about 20 percent of all mamma carcinoma patients, the HER-2 receptor protein is over-expressed on the surface of cancer cells. Herceptin, a monoclonal antibody, binds selectively to parts of the HER-2 receptor and blocks it, so that no growth signals are derived there from. With HER-2 negative tumors, however, no or too few target sites exist for the antibody. The growth of these cells is influenced so little by the antibody that blockade of the receptor has no effect; these patients do not benefit from this therapy.

U.S. Pat. No. 6,653,292 discloses a concept to treat tumor diseases by combining cytokines, for example GM-CSF, with chemotherapeutic measures or combining immune stimulatory, CpG-containing oligonucleotides with chemotherapy. In-vivo and in-vitro data or clinical results demonstrating the efficacy of the claimed combinations, however, cannot be shown there.

The CpG oligonucleotides, which are employed in both cases, are protected by phosphothioate residues on both ends in order to protect them from digestion by cellular enzymes. In clinical studies, however, it was shown that these thioate compounds impart significant adverse side effects, mainly on the blood clotting system and the complement system (Sheehan et al., 1998, Blood 92: 1617-1625). In rhesus macaques, severe toxicity of thioate-protected CpG oligonucleotides was demonstrated, which was due to activation of the complement system (Henry et al., 2002, Int. Immunopharmacol 2: 1657). In addition, thioate modifications led to a significant enlargement of the spleen, to destruction of lymphatic vesicles and immune suppression after repeated application in mice (Heikenwalder et al., 2004, Nat. Med. 10: 187).

These severe side effects allow the use of thioate-protected CpG oligonucleotides in tumor therapy only with great reservations.

Figure 1A:
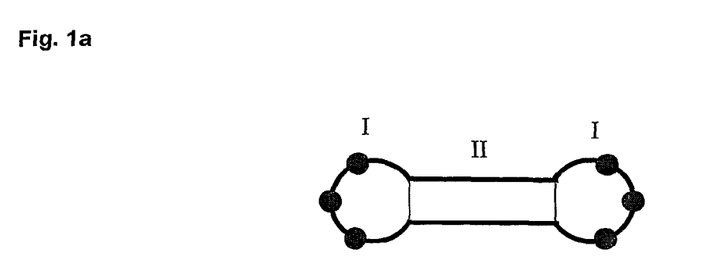
Figure 1B:
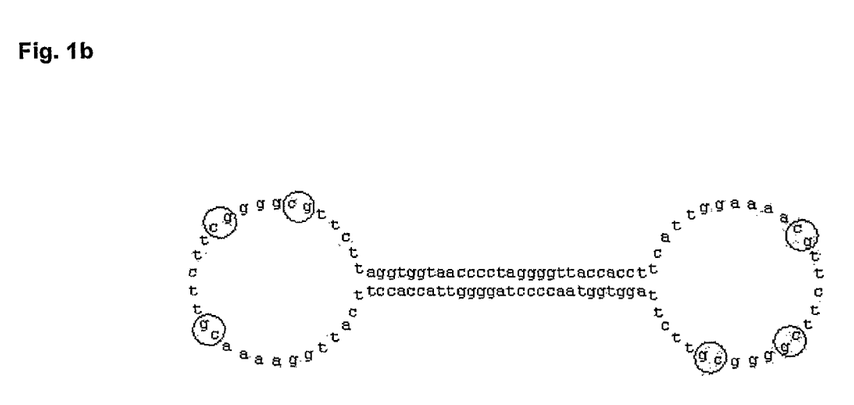

Furthermore, immune stimulatory nucleic acid sequences (ISS) that also contain CpG motifs, are only few bases in length and do not exert their effect by the expression proteins encoded thereon, are known from EP 1 196 178 B1. These are dumbbell-shaped deoxyribonucleic acid molecules. They consist of oligonucleotides, the bases of which can partially hybridize with each other, and one or two hairpin loops comprising 30 bases and containing several CpG motifs (see FIG. 1). The teaching of the use and production of immune stimulatory, CpG-containing ISS is disclosed in detail in EP 1 196 178 B1. The covalently closed deoxyribonucleic acid molecules can be advantageously made from open chain deoxyribonucleic acid molecules that comprise a partially self complementary sequence and can form a intermediately stable molecule with each other or with a second molecule. Favourably, the molecule can be made by intramolecular ligation of a molecule that comprises at least two self complementary regions, which are separated by a gap in the phosphate. Molecules thus obtained do not comprise free 5' or 3' terminal OH ends and are thus not accessible for exonucleases.

Preferentially, the immune modulating deoxyribonucleotide comprises a sequence of the base sequence $N^1N^2CGN^3N^4$, where $N^1N^2$ is an element chosen from the group comprising GT, GG, GA, AT or AA, $N^3N^4$ an element chosen from the group comprising CT or TT, and C is deoxycytosine, G is deoxyguanosine, A is deoxyadenosine and T is deoxythymidine. Preferentially, the sequence of the base sequence $N^1N^2CGN^3N^4$ is positioned in the single-stranded region of the deoxyribonucleotide and the deoxyribonucleotide comprises 40 to 200 nucleotides.

In spite of research over many years and promising approaches, it has not been possible to develop an efficacious therapy against the majority of common tumor diseases.

In the light of this state of the art, it is the objective of the present invention to provide a pharmaceutical composition for the treatment of tumor diseases, which leads to an induction of a tumor-specific humoral and cellular immune response.

Solution According to the Invention and Advantages of the Invention

The fundamental problem in tumor recognition by the body's immune system is that tumors, in contrast to most micro-organisms, do not induce an inflammatory reaction. Therefore, the signal for the immune system to start the immune reaction is missing. Tumor cells can not be recognized as aberrant cells and therefore, are able to grow and multiply unhindered.

The necrotic decay of the tumor cells, which is a consequence of the chemo therapy, liberates cell debris and molecular particles from the cytoplasma. These liberated structures, also termed tumor antigens, represent important structures for targeting and recognition for the attack of the immune system against residual tumor or tumor cells that have spread into the body. As a consequence of measures of chemotherapy or radiation therapy with very toxic cytostatic drugs, a great number of antigens are present in the body, caused by the onset of necrosis. The innate immune system has no evolutionary imparted specificity for these structures, as it has for microbes or other external agents of disease. Therefore, tumor-related antigenic structures are not or insufficiently recognized by innate components of immunity. This in turn causes tumor antigens to not be attacked efficiently by the innate immune system. Since the adaptive immune system is not triggered by tumor antigens in the absence of necessary co-factors such as inflammatory signals, no specific immune response against tumor antigens is elicited.

This problem is solved by the inventive use of immune modulators on the basis of DNA and the inventive combination vaccine.

The invention makes use of the fact that an unspecific immune response can be switched into a specific adaptive immune response if the antigens are present, against which the specific immune response is to be mounted.

By supplying immune modulators on the basis of DNA, the immune system is led to react in a fashion as if an infection had taken place, which it had not in reality. As a consequence, cells, mainly thymocytes that possess a helper function and cytotoxic thymocytes, B cells and so-called NK (natural killer) cells, macrophages and monocytes, as well as dendritic cells and their precursors, as well as functionally as yet unexplained cell populations with functions within the immune system, are stimulated to proliferate, migrate, differentiate or become active and induced to translocate to the site of infection. These different immune cells, whether newly formed in the processes described above or induced to migrate by signal substances, however do not find any infective agent at the presumed site of infection. These cells will then commence to engage in phagocytosis of the tumor antigens, in lieu of the infective agents that are not present, and present them as molecular fragments to the adaptive immune system. By this pathway, the adaptive immune system learns to recognise the molecular recognition and targeting structures of tumor cells and produces ever more specific immune cells against them. In this fashion, the immune system is enabled to produce cells of defence and destruction against these tumors also for the future.

The immune modulators on the basis of DNA lead to the generation of memory antigens, so called recall antigens. Mediated through special immune cells, the immune system can remember these antigens, and a new cellular response is triggered upon renewed contact (see FIG. 7).

The invention therefore relates to the novel use of immune modulators on the basis of DNA according to claim 1 and the following claims and to the production of a pharmaceutical substance, which is applied in combination with chemotherapeutic drugs in the therapy of neoplastic disease.

The immune modulators on the basis of DNA are dumbbell-shaped, covalently closed deoxyribonucleic acid molecules that comprise CpG motifs.

The immune modulating effect of the dumbbell-shaped, covalently closed deoxyribonucleic acid molecules is strongly dependent on the combination of loop and double strand and the contained CpG motifs. Linearisation, deletion of a hairpin loop, downsizing of the molecule or the removal of CpG motifs all lead to a change in the cytokine induction pattern.

According to the invention, oligodeoxyribonucleotides are used, where the immune stimulating oligodeoxyribonucleotide comprises a) a sequence comprising the base sequence $N^1N^2CGN^3N^4$, where $N^1N^2$ is an element chosen from the group comprising GT, GG, GA, AT or AA, $N^3N^4$ is an element chosen from the group comprising CT or TT, and C is deoxycytosine, G is deoxyguanosine, A is deoxyadenosine and T is deoxythymidine, b) and a circular strand of deoxyribonucleic acid with a partially complementary anti-parallel base sequence and is of dumbbell-shaped form.

The sequence with the base sequence $N^1N^2CGN^3N^4$ is positioned in the single stranded region of the oligodeoxyribonucleoside and comprises 40 to 200 nucleotides.

The immune modulating deoxyribonucleotides as described in EP 1 196 178 B1 are of advantage. It was neither disclosed nor could it be expected that these immune modulating deoxyribonucleic acid molecules are useful for serving the purpose of stimulating the human immune system as a preparatory measure in the event of a diagnosis relating to a malign neoplastic disease with concurrently indicated application of cytostatic drugs.

In the context of the invention disclosed herein, the following terms are to be interpreted as follows:

A "patient" for the purposes of the present invention includes both humans and other animals, particularly mammals, and other organisms. Thus the methods are applicable to both human therapy and veterinary applications. In the preferred embodiment the patient is a mammal, and in the most preferred embodiment the patient is human.

The term "animal" refers to an organism with a closed circulatory system of blood vessels and includes birds, mammals and crocodiles. The term "animal" used here also includes human subjects.

The term "angiogenesis" refers to the generation of new blood vessels into cells, tissue, organs or tumors.

The term "metastasis" refers to the process by which tumor cells are spread to distant parts of the body. The term is also used herein to refer to a tumor that develops through the metastatic process.

The term "contacting" is used herein interchangeably with the following: combined with, added to, mixed with, passed over, incubated with, flowed over, etc. Moreover, the compounds of present invention can be "administered" by any conventional method such as, for example, parenteral, oral, topical and inhalation routes as described herein.

As used herein, the term "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer, either a sarcoma or lymphoma, to shrink or not metastasize. The specific safe and effective amount or therapeutically effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

"An anti-angeogenic" amount refer to an amount of a compound or composition effective to depress, suppress or inhibit angiogenesis or result in amelioration of symptoms associated with an angiogenic disease. The desired result can be either a subjective relief of a symptom(s) or an objectively identifiable improvement in the recipient of the dosage, a decrease in the vascularization of endothelial cells or a decrease in the rate of angiogenesis as noted by a clinician or other qualified observer.

The terms "treating cancer," "therapy," and the like refer generally to any improvement in the mammal having the cancer wherein the improvement can be ascribed to treatment with the compounds of the present invention. The improvement can be either subjective or objective. For example, if the mammal is human, the patient may note improved vigor or vitality or decreased pain as subjective symptoms of improvement or response to therapy. Alternatively, the clinician may notice decrease in tumor size or tumor burden based on physical exam, laboratory parameters, tumor markers or radiographic findings. Some laboratory signs that the clinician may observe for response to therapy include normalization of tests such as white blood cell count, red blood cell count, platelet count, erythrocyte sedimentation rate, and various enzyme levels. Additionally, the clinician may observe a decrease in a detectable tumor marker. Alternatively, other tests can be used to evaluate objective improvement such as sonograms, nuclear magnetic resonance testing and positron emissions testing.

"Inhibiting the growth of tumor cells" can be evaluated by any accepted method of measuring whether growth of the tumor cells has been slowed or diminished. This includes direct observation and indirect evaluation such as subjective symptoms or objective signs as discussed above.

Accordingly, the compositions of the invention are administered to cells. By "administered" herein is meant administration of a therapeutically effective dose of the candidate agents of the invention to a cell either in cell culture or in a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art. By "cells" herein is meant almost any cell in which mitosis or meiosis can be altered.

In the context of the present invention, the term "treatment" means the prophylactic and/or therapeutic effect of a pharmaceutical compound.

Immune stimulation/immune modulation means the therapeutic manipulation of the immune reaction, that is the propensity of the organism to mount a defense. The objective of such therapy is to fight the tumor with means facilitated by the body. Chemotherapy is the systematic pharmaceutical therapy of tumor diseases with so called cytostatic drugs.

In the context of the present invention, the term chemotherapeutic relates to cytostatic drugs that are usually applied in adjuvant, palliative and curative tumor therapy. These include for example, but are not limited to, the following:

Compounds from the group of topoismomerase inhibitors, for example Irinotecan, Topotecan,
from the group of alkylating agents, for example Busulfane, Dacarbazine
from the group of platin compounds, for example cisplatin, carboplatin or oxaliplatin,
from the group of antimetabolite compounds, for example Methotrexate, 5-Fluoruracil, Mercaptopurine or Cytarabine,
from the group of antracycline and actinimycine compounds, for example Mitoxantrone and Amsacrine,
from the group of vinca alkaloids, for example Vinorelbine,
from the group of taxane compounds, for example Paclitaxel and Docetaxel,
from the group of anti-estrogenic compounds, for example Tamoxifene, Following, more detailed cancer chemotherapeutics are shown. They are characterized in different groups, depending from their chemical nature or their physiological impact to the organism, namely ALKYLATING AGENTS
ANTIMETABOLITES
ANTIBIOTICS
MITOTIC INHIBITORS
CHROMATIN FUNCTION INHIBITORS
HORMONES AND HORMONE INHIBITORS

IMMUNOMODULATORS
MISCELLANEOUS

The group of ALKYLATING AGENTS comprises the following agents:

I. NITROGEN MUSTARDS
mechlorethamine (Mustargen)
cyclophosphamide (Cytoxan, Neosar)
ifosfamide (Ifex)
phenylalanine mustard; melphalen (Alkeran)
chlorambucol (Leukeran)
uracil mustard
estramustine (Emcyt)
II. ETHYLENIMINES
thiotepa (Thioplex)
III. ALKYL SULFONATES
busulfan (Myerlan)
IV. NITROSUREAS
lomustine (CeeNU)
carmustine (BiCNU, BCNU)
streptozocin (Zanosar)
V. TRIAZENES
dacarbazine (DTIC-Dome)
VI. PLATINUM COORDINATION COMPLEXES
cis-platinum, cisplatin (Platinol, Platinol AQ)
carboplatin (Paraplatin)
VII. OTHERS
altretamine (Hexalen)

The group of ANTIMETABOLITES comprises the following agents

I. FOLIC ACID ANALOGS
methotrexate (Amethopterin, Folex, Mexate, Rheumatrex)
II. PYRIMIDINE ANALOGS
5-fluoruracil (Adrucil, Efudex, Fluoroplex)
floxuridine, 5-fluorodeoxyuridine (FUDR)
capecitabine (Xeloda)
fludarabine: (Fludara)
cytosine arabinoside (Cytaribine, Cytosar, ARA-C)
II. PURINE ANALOGS
6-mercaptopurine (Purinethol)
6-thioguanine (Thioguanine)
gemcitabine (Gemzar)
cladribine (Leustatin)
deoxycoformycin; pentostatin (Nipent)

The group of ANTIBIOTICS comprises the following agents
doxorubicin (Adriamycin, Rubex, Doxil, Daunoxome-liposomal preparation)
daunorubicin (Daunomycin, Cerubidine)
idarubicin (Idamycin)
valrubicin (Valstar)
mitoxantrone (Novantrone)
dactinomycin (Actinomycin D, Cosmegen)
mithramycin, plicamycin (Mithracin)
mitomycin C (Mutamycin)
bleomycin (Blenoxane)
procarbazine (Matulane)

The group of MITOTIC INHIBITORS comprises the following agents

I. TAXANES (DITERPENES)
paclitaxel (Taxol)
docetaxel (Taxotere)
II. VINCA ALKALOIDS
vinblatine sulfate (Velban, Velsar, VLB)
vincristine sulfate (Oncovin, Vincasar PFS, Vincrex)
vinorelbine sulfate (Navelbine)

The group of CHROMATIN FUNCTION INHIBITORS comprises the following agents

I. CAMPTOTHECINS
topotecan (Camptosar)
irinotecan (Hycamtin)
II. EPIPODOPHYLLOTOXINS
etoposide (VP-16, VePesid, Toposar)
teniposide (VM-26, Vumon)

The group of HORMONES AND HORMONE INHIBITORS comprises the following agents

I. ESTROGENS
diethylstilbesterol (Stilbesterol, Stilphostrol)
estradiol, estrogen (many brands)
esterified estrogens (Estratab, Menest)
estramustine (Emcyt)
II. ANTIESTROGENS
tamoxifen (Nolvadex)
toremifene (Fareston)
II. AROMATASE INHIBITORS
anastrozole (Arimidex)
letrozole (Femara)
III. PROGESTINS
17-OH-progesterone (many brands)
medroxyprogesterone (many brands)
megestrol acetate (Megace)
IV. GnRH AGONISTS
goserelin (Zoladex)
leuprolide (Lupron)
V. ANDROGENS
testosteraone (many brands)
methyltestosterone (many brands)
fluoxmesterone (Android-F, Halotestin)
VI. ANTIANDROGENS
flutamide (Eulexin)
bicalutamide (Casodex)
nilutamide (Nilandron)
VII. INHIBITORS OF SYNTHESIS
aminoglutethimide (Cytadren)
ketoconazole (Nizoral)

The group of IMMUNOMODULATORS comprises the following agents
rituximab (Rituxan)
trastuzumab (Herceptin)
denileukin diftitox (Ontak)
levamisole (Ergamisol)
bacillus Calmette-Guerin, BCG (TheraCys, TICE BCG)
interferon alpha-2a, alpha 2b (Roferon-A, Intron A)
interleukin-2, aldesleukin (ProLeukin)

Further, several MISCELLANEOUS chemotherapeutics are know and herewith shown:
I-aspariginase (Elspar, Kidrolase)
pegaspasgase (Oncaspar)
hydroxyurea (Hydrea, Doxia)
leucovorin (Wellcovorin)
mitotane (Lysodren)
porfimer (Photofrin)
tretinoin (Veasnoid)

All the foregoing cancer chemotherapeutics are part and object of the invention. Furthermore, the scope of the invention also includes further cytostatic drugs that are employed in chemotherapy, and which are not explicitly stated above. Cytostatic drugs or combinations thereof are preferred that are applied to a patient in a single cycle.

The compositions and methods provided herein are particularly deemed useful for the treatment of cancer including solid tumors such as skin, breast, brain, cervical carcinomas, testicular carcinomas, etc. More particularly, cancers that may be treated by the compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adeno-carcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above identified conditions.

Therefore, as used herein, "cancer" refers to all types of cancer or neoplasm or malignant tumors found in mammals, including carcinomas and sarcomas. Examples of cancers are cancer of the brain, breast, cervix, colon, head & neck, kidney, lung, non-small cell lung, melanoma, mesothelioma, ovary, sarcoma, stomach, uterus and Medulloblastoma.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The P388 leukemia model is widely accepted as being predictive of in vivo anti-leukemic activity. It is believed that compound that tests positive in the P388 assay will generally exhibit some level of anti-leukemic activity in vivo regardless of the type of leukemia being treated. Accordingly, the present invention includes a method of treating leukemia, and, preferably, a method of treating acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with ester of the invention and optionally a potentiator and/or chemotherapeutic agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with said esters and optionally a potentiator and/or another chemotherapeutic agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with said ester and optionally a potentiator and/or a chemotherapeutic agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

Additional cancers which can be treated with ester according to the invention include, for example, Hodgkin's Disease, Non-Hodgkin's Lymphoma, multiple mycloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, unnary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

The term tumor disease or neoplastic disease includes therefore carcinogenic metastasing diseases from the group of cervix carcinoma, mamma carcinoma, colorectal and rectal carcinoma, primary liver cell carcinoma, prostate carcinoma, non-small cell bronchial carcinoma (NSCLC), pancreatic carcinoma, bladder carcinoma, ovarian carcinoma and further cancerous diseases that are not mentioned.

The vaccine that is a result of the novel inventive use is provided to patients, to be injected into the skin, below the skin and into the muscle.

The application of deoxyribonucleic acid molecules according to claim 1 and following claims in the immediate time prior to beginning a therapy with cytostatic drugs on the patient, leads to an increased concentration of soluble, proliferation stimulating cytokines and co-stimulatory molecules at the site of application as a consequence of the induced immune reaction, in conjunction with tumor-associated antigens (TAA), which leads to activation and proliferation of tumor-specific T-cells.

Furthermore, as a consequence of the injections with deoxyribonucleic acid molecules according to claim 1 and following claims, antigen presenting cells (APC) and dendritic cells (DC) are enticed to migrate towards the site of application. The presence of these two cell types has a synergistic effect on the presentation of TAA, and the increased presentation of TAA in turn has an effect on the activated cytotoxic T-lymphocytes, which are formed increasingly.

Figure 2:
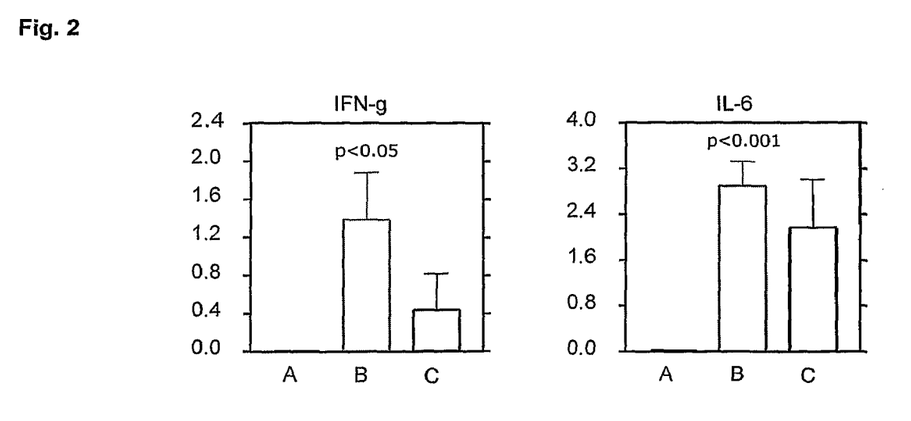
FIG. 2: shows the secretion of cytokines interferon gamma in interleukin-6 after in-vitro stimulation of peripheric blood monocytes (PBMCs) by:
  A: negative control, buffer
  B: immune modulators on the basis of DNA
  C: linear, thioate-protected CpG oligonucleotides.
Figure 3:
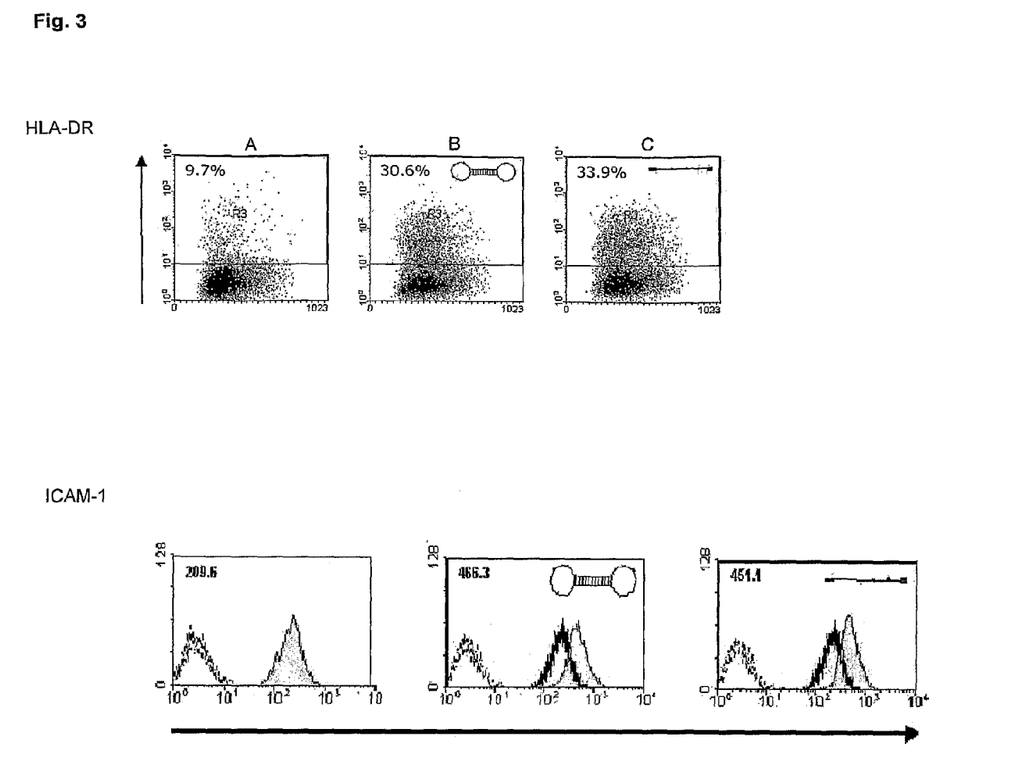
FIG. 3: shows the expression of the immune relevant surface molecules HLA-DR and ICAM-1 after in-vitro stimulation of B-lymphocytes by:
  A: negative control, buffer
  B: immune modulators on the basis of DNA
  C: linear, thioate-protected CpG oligonucleotides.

Furthermore, the injection of deoxyribonucleic acid molecules according to claim 1 and following claims leads to the expression of immune-relevant surface molecules on the tumor cells, including ICAM-1, HLA-DR, CD80 and CD40. The adhesion molecule ICAM-1 leads to the activation of effector T-helper cells. Concerning HLA-DR, it could be demonstrated that the density of expression on monocytes is a reliable surrogate marker for the ability of the monocytes to react by liberating proinflammatory cytokines (for example tumor necrosis factor alpha, IL-1, IL-6, IL-8). It was demonstrated in-vitro that deoxyribonucleic acid molecules according to claim 1 and following claims leads to the formation of interferon gamma and interleukin 6, another important stimulator of the immune response and hematopoieses (see FIG. 2). The increased expression of ICAM-1 and HLA-DR on B-lymphocytes is shown in FIG. 3.

Furthermore, deoxyribonucleic acid molecules according to claim 1 and following claims cause an increased proliferation of B lymphocytes, the carrier cells of the humoral immune response. B lymphocytes either differentiate into antibody-producing plasma cells or to memory cells, which switch to antibody production directly upon renewed contact with previously encountered antigen. It was shown that deoxyribonucleic acid molecules according to claim 1 and following claims lead to an increased secretion of immunoglobulins IgM, IgA and IgG (see FIG. 4). Antibody isotypes IgG1 and IgG2 were determined as well in order to demonstrate a possible Th2/Th1 shift in the immune response bias. The isotype distribution of immunoglobulin gamma (IgG) for a given antigen mirrors the bias of the complete immune reaction against this antigen. IgG1 subtypes are characteristic for a humoral response, accompanied by increased secretion of interleukins IL-4 and IL-10 by activated lymphocytes. An increased level of subtype IgG2 is typical for a cellular Th1 response, accompanied by increased secretion of IFN gamma and IL-12.

Figure 5A:
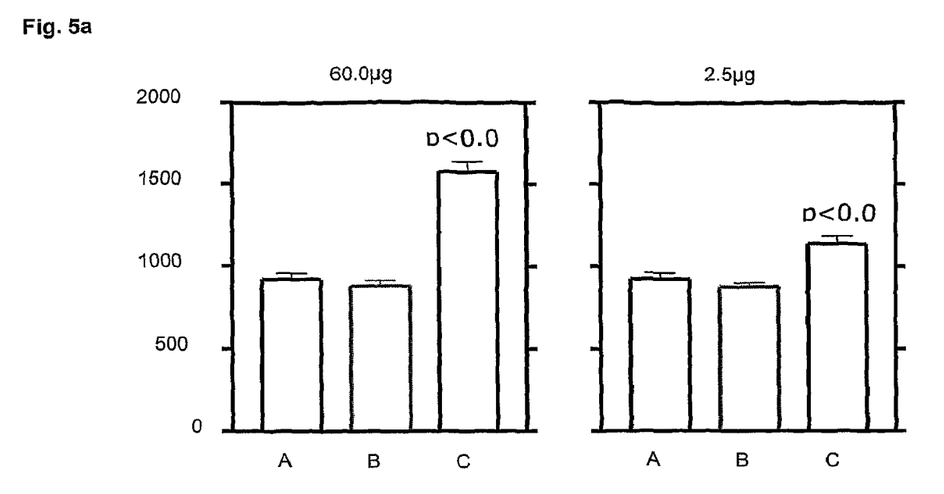
FIG. 5a: it was determined whether immune modulators on the basis of DNA as specified in the present invention and the thioate-protected CpG oligonucleotides can have a toxic effect on the organism. This determination was performed by measuring the increase in weight of the internal organs liver, spleen and lymph nodes in mouse experiments.
  A: negative control, buffer
  B: immune modulators on the basis of DNA
  C: linear, thioate-protected CpG oligonucleotides
were administered to mice. The negative control served as a base value. Immune modulators on the basis of DNA as specified in the present invention B do not lead to an increase of liver size, independent of applied amount. Thioate-protected CpG oligonucleotides, however, lead to a significant liver enlargement even for the small amount of 60 micrograms.
Figure 5B:
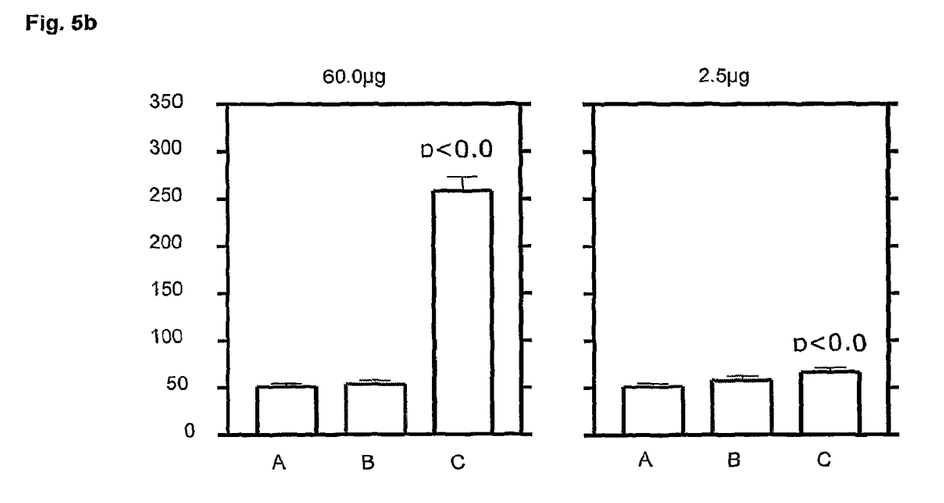
Figure 5C:
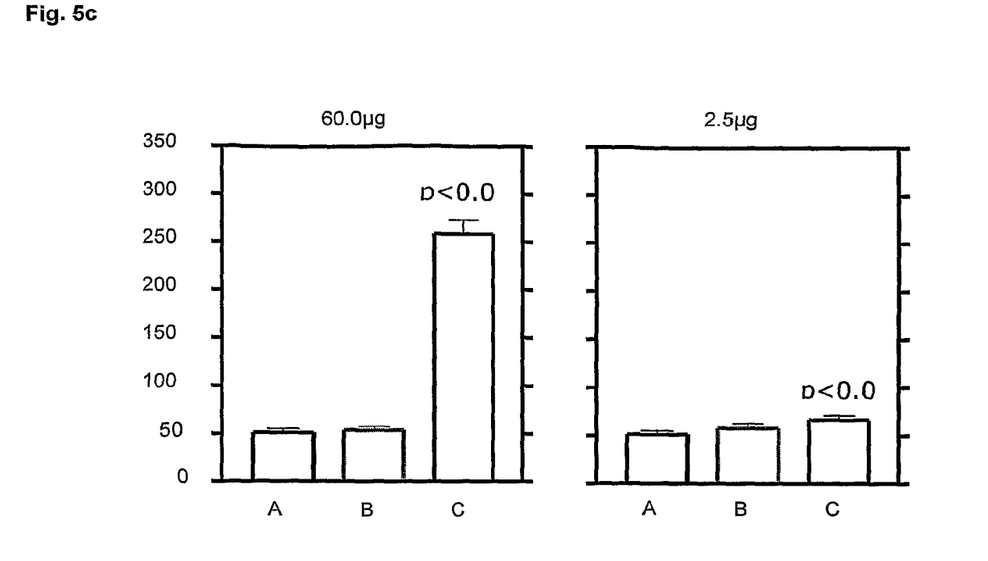
FIG. 5c: The influence of B and C on the lymph nodes was determined.

In contrast to the known linear, thioate-protected oligonucleotides that contain CpG motifs, the deoxyribonucleic acid molecules according to claim 1 and following claims employed herein show a number of advantages. They do not lead to an increased organ size, shown in the example of the organs liver, spleen and lymph nodes in mice comparing the two compounds (see FIG. 5). As another advantage, no anomalies occurring in these organs could be demonstrated in the experimental period.

Figure 6:
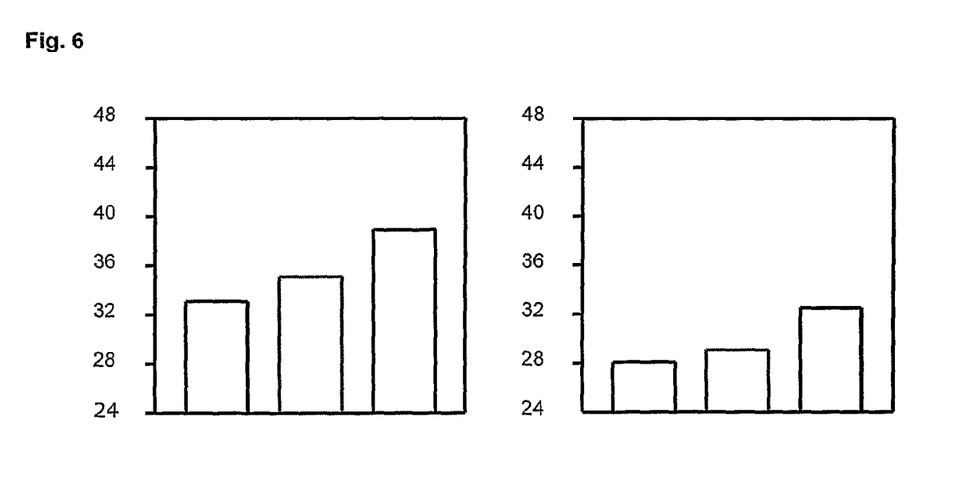
FIG. 6: shows another analysis of the toxic effect of application of the immune modulators on the basis of DNA in comparison to thioate-protected CpG oligonucleotides. The parameter in question was the prolongation of blood clotting time. The two graphs are related to different donors. Partial thromboplastine time in seconds is given on the ordinate.

Furthermore, the inventive molecules do not lead to the prolongation of blood clotting time as a consequence of the treatment (see FIG. 6). An increase of blood clotting time would lead to a prolonged duration of bleeding in case of external lesions, nose bleeding, gingival bleeding or microlesions caused by the intake of food on the gastro-intestinal mucosa and in the case of surgical procedures. Furthermore, the danger if internal bleeding would have to be taken into account, which may be diagnosed too late.

The invention also relates to a kit and to the use thereof in medicine. In a preferred fashion, the compounds of the invention or the kit comprising same is used in a combination therapy, especially in the treatment of tumors. In a particularly preferred fashion, said combination therapy comprises a chemotherapy, a treatment with cytostatic agents and/or a radiotherapy. In a particularly preferred embodiment of the invention the combination therapy is a biologically specific form of therapy, and in a particularly preferred fashion, said form of therapy is an immune therapy. Furthermore, in a particularly preferred fashion the combination therapy comprises a gene therapy and/or a therapy using a compound according to the invention. Various combination therapies, especially for the treatment of tumors, are well-known to those skilled in the art. For example, a treatment with cytostatic agents or irradiation of a particular tumor area can be envisaged within the scope of a combination therapy, and this treatment is combined with a gene therapy, using the compounds of the invention as anticancer agents. Furthermore, a preferred use of the compounds according to the invention is in inhibiting the vitality, the proliferation rate of cells and/or inducing apoptosis and cell cycle arrest.

Therefore, the further object of the invention is a kit, comprising, in suitable container means, the immune modulators on the basis of DNA in the form of dumbbell-shaped, covalently closed immune modulating deoxyribonucleic acid molecules, and a cytostatic (chemotherapeutic) drug or compositions thereof and an information about the using of parts of the kit. Said information can also be related to a diagnostic or therapeutic scheme. The essentials, resp. parts of the kit are used although sequential whereby therapeutically amounts of the parts of the kit are administered to a cancer patient sequential within 0 between 72 hours. The kit, resp. parts of the kit are useful for the treatment of cancer, angiogenesis.

In summary, it can be stated that the application of deoxyribonucleic acid molecules according to claim 1 and following claims in the time leading up to a chemotherapy will lead to increased expression of surface antigens in tumor cells and thus renders tumor cells better recognizable to the immune system. Furthermore, receptors for important immune cells are activated, among them NK cells, that enhance the ability of the immune system to fight tumor cells. Furthermore, the increased synthesis of antibodies that can also destroy tumor cells can be observed. Local interactions between antigen presenting cells and effector cells, such as natural killer cells (NK cells) and T lymphocytes are important for an effective immune reaction against tumors.

Further advantageous forms of the invention can be derived from the dependent claims and the description. The surprising effect of the inventive pharmaceutical for tumor therapy as well as the inventive method is disclosed in the tables and the examples; in detail it is shown in FIG. 1a and 1b: Schematically representation of covalently closed, immune modulating oligodesoxynucleotides that contain CpG motifs: dumbbell-shaped structure with three CpG motifs depicted as a dark circle in the hairpin region of the loop; numbers mean I: loop and II: stem.

The negative control leads to no secretion of interferon gamma or interleukin-6, as was expected. Both molecules B and C are capable to stimulate PBMCs to secrete cytokines. The secretion of interferon gamma is increased 2.5 fold by B in comparison to C. This tendency of a significantly increased secretion in comparison to C can also be observed for the cytokine interleukin-6.

The negative control leads to no secretion of HLA-DR or ICAM-1, as was expected. The stated values of 9.7% and 209.6, respectively, are employed as base values for the determination of the median fluorescence intensity for non-stimulated positive cells. Both molecules B and C lead to a stimulation of both surface molecules, giving approximately similar results for B and C.

Figure 4:
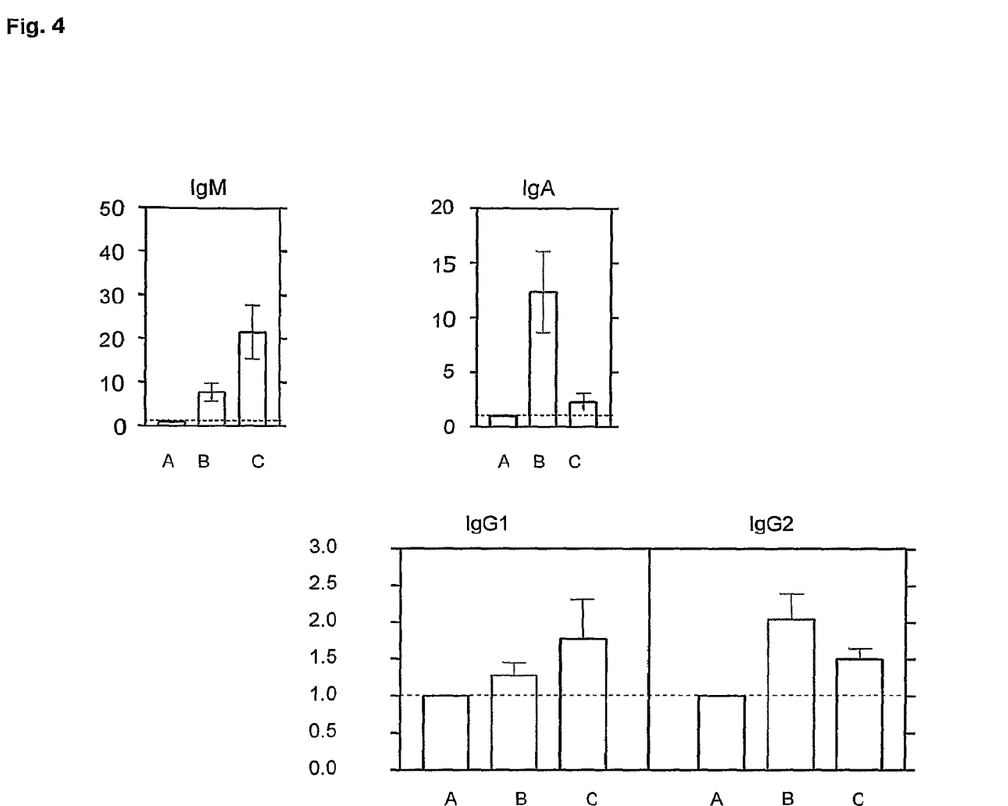
FIG. 4: shows increased antibody production after in-vitro stimulation of peripheric blood monocytes (PBMCs) by:
  A: negative control, buffer
  B: immune modulators on the basis of DNA
  C: linear, thioate-protected CpG oligonucleotides.

The negative control leads to no secretion of IgM, IgA, IgG1 and IgG2, as was expected. B and C lead to a significantly increased stimulation of antibody production, where IgA secretion is increased 3-fold for B in comparison to C. The relative titers of isotypes IgG1 and IgG2 can be taken as an indicator for the dominant type of immune response. The ratio of IgG2 and IgG1 shows that immune modulators on the basis of DNA as specified in the present invention can provoke a cytotoxic immune response (Th1) in addition to a humoral response.

FIG. 5b: The influence of B and C on the spleen was determined.
  A: negative control, buffer
  B: immune modulators on the basis of DNA
  C: linear, thioate-protected CpG oligonucleotides
were administered to mice. The negative control served as a base value. Immune modulators on the basis of DNA as specified in the present invention B do not lead to an increase of spleen size, independent of applied amount. Thioate-protected CpG oligonucleotides, however, lead to a significant spleen enlargement even for the small amount of 60 micrograms, reflecting an increase of the factor five in comparison to the values of A or B.

A: negative control, buffer
B: immune modulators on the basis of DNA
C: linear, thioate-protected CpG oligonucleotides were administered to mice. The negative control served as a base value. Immune modulators on the basis of DNA as specified in the present invention B do not lead to an increase of lymph node size, independent of applied amount. Thioate-protected CpG oligonucleotides, however, lead to a significant lymph node enlargement even for the small amount of 60 micrograms, reflecting an increase of the factor two in comparison to the values of A or B.

A: negative control, buffer
B: immune modulators on the basis of DNA
C: linear, thioate-protected CpG oligonucleotides were applied. Immune modulators on the basis of DNA as specified in the present invention B showed no prolongation of blood clotting time in both experiments when compared to a negative control. The thioate-protected CpG oligodeoxynucleotides led to a significantly increased prolongation of blood clotting time in comparison to the negative control and B.

Figure 7:
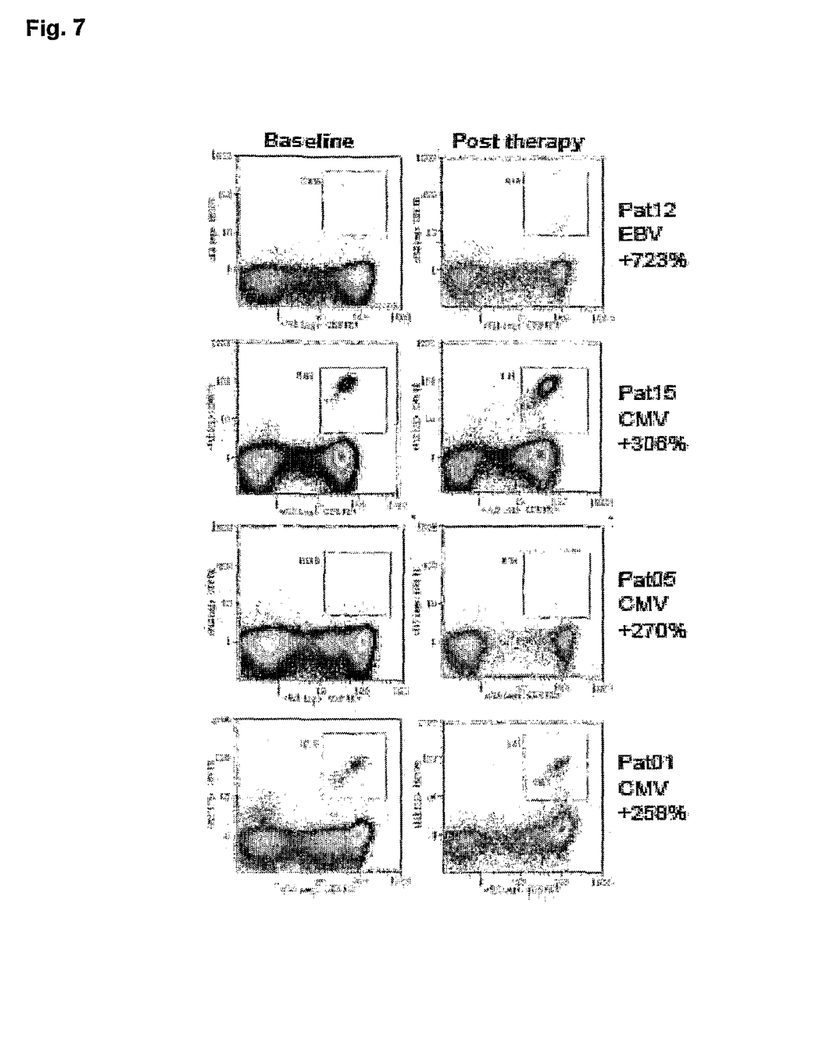
FIG. 7: shows recall antigens of four patients after a cycle of chemotherapy.

All patients were in an advanced state of the disease at the beginning of treatment. In order to determine a clinical success, the following terms according to the World Health Organization (1979) shall apply: a partial response (PR) is a reduction of ascertainable tumor foci by more than 50% over the last four weeks and a suppression of new tumor foci. Stable disease (SD) is the continuation of the state. A mixed response (MR) is a mixed reaction, for instance the progression of metastasizing and a reduction of metastases in another place. A complete response (CR) is the complete remission of tumor foci.

Selection of patients: patients with cervical carcinoma, mamma carcinoma, colorectal and rectal carcinoma, primary liver cell carcinoma, prostate carcinoma, non-small cell bronchial carcinoma (NSCLC), pancreatic carcinoma, urinary bladder carcinoma and ovarian carcinoma, aged 18 to 70 years and a Karnofsky index of 70-100 were eligible for inclusion. Criteria for refusal were: a previous treatment with cytokines or chemotherapy less than 28 prior, creatine values of above 265 micromole/l, bilirubin values of above 51 micromole/l, non-compensated cardiac insufficiency, ventricular dysrhythmia, severe psychiatric disorder, active hepatitis A, B or C, HIV infection.

Treatment: apart from anamnesis, the following parameters were determined prior to treatment: physical examination, hematology (haemoglobin, hematocrit, leukocytes and platelet count), and chemical analysis of blood and urine analysis. Blood was taken to determine immune status. DHT (delayed type hypersensitivity) skin tests were performed with Multitest Merieux assay (Leimen, Germany). X-ray scans and computer tomography of the upper body and abdomen were performed. Comprehensive immunological examination, hematological assays and cursory clinical examination (physical examination, ultrasound examination and examination of the lower body, where appropriate) were repeatedly performed. A complete clinical and immunological examination comparable to the examination performed prior to registration was performed at the end of every cycle of treatment.

It is provided according to the invention that patients receive injections of 500 micrograms of deoxyribonucleic acid molecules according to claim 1 and the following claims into the skin, subcutaneously and into the muscle. Patients receive five times two injections of 500 micrograms of deoxyribonucleic acid molecules according to claim 1 and the following claims in the period around the respective cycle of chemotherapy, in preset intervals of two to eight days. The total amount of applied deoxyribonucleic acid molecules according to claim 1 and the following claims varies between 1 and 10 milligrams.

The two injections were performed on the first day of injection into the into the typical sites of vaccination in the skin (intradermal) laterally on the left and right upper arm, on the second day intradermal on the upper portion of the left and right upper thigh, on the third day subcutaneously about 30 mm left and right of the navel, on day four into the described sites on the upper arm, but subcutaneously, and on day five intramuscularly into the front side of the left and right upper thigh.

Injection scheme for the treatment of metastasizing mamma carcinoma:

| Time of injection | compound | Site of application | Method of application |
|---|---|---|---|
| −10 | 1 mg of the immune modulator on basis of DNA (1 mg/ml) | 2 × 0.5 mg left a. right upper arm | intradermal |
| −7 | 1 mg of the immune modulator on basis of DNA (1 mg/ml) | 2 × 0.5 mg left a. right thigh | intradermal |
| −4 | 1 mg of the immune modulator on basis of DNA (1 mg/ml) | 2 × 0.5 mg left a. right of the navel | subcutaneously |
| −2 | 1 mg of the immune modulator on basis of DNA (1 mg/ml) | 2 × 0.5 mg left a. right upper arm | subcutaneously |
| −1 | 1 mg of the immune modulator on basis of DNA (1 mg/ml) | 2 × 0.5 mg left a. right thigh | intramuscularly |
| 0 | 1 mg Gemcitabine | | |

The time of injection is given relative to the onset of chemotherapy (day zero) with Gemcitabine.

Up to 50 ml blood is taken for concurrent diagnostic procedures prior to beginning the treatment and before each injection.

Patients with metastasizing cervical carcinoma were treated with radiation after injection of deoxyribonucleic acid molecules according to claim 1 and the following claims.

Patients with metastasizing mamma carcinoma were treated with the common chemotherapeutic drugs Gemcitabine or Xeloda after injection of deoxyribonucleic acid molecules according to claim 1 and the following claims. Also, the use of anthracyclines (Epirubicin, Doxorubicin, Mitoxanthrane) in combination with deoxyribonucleic acid molecules according to claim 1 and the following claims is provided.

Patients with metastasizing primary liver carcinoma and prostate carcinoma were treated palliatively with a combination of deoxyribonucleic acid molecules according to claim 1 and the following claims and Taxotere, or deoxyribonucleic acid molecules according to claim 1 and the following claims and Mitoxanthron.

Patients suffering from metastasizing rectal or colorectal carcinoma were treated by adjuvant or palliative therapy after injection of deoxyribonucleic acid molecules according to claim 1 and the following claims with a combination of cytostatic drugs Leucovorine and 5-Fluorouracil (5-FU). The combination of FOLFOX 4 (Oxaliplatin, folinic acid and 5-Fluorouracil) and FOLFIRI (Irinotecan, folinic acid and 5-Fluorouracil) after the injection of deoxyribonucleic acid molecules according to claim 1 and the following claims is also provided.

All treatments are conducted according to preset cycles. It is provided to conduct only one cycle of the combination comprising the treatment with deoxyribonucleic acid molecules and subsequent chemotherapy. If another treatment is necessary after the end of the chemotherapy cycle, this treatment is continued with further injections of deoxyribonucleic acid molecules according to claim 1 and the following claims. Immunotherapeutic approaches may be continued in the same fashion. An immediately subsequent commencement of chemotherapy does not seem indicated from a medical point of view, but is not excluded. It may seem justified and in certain cases indicated to continue the treatment after six months, which is interpreted as another application of the inventive vaccine, according to the invention.

EXAMPLE 1

Synthesis of Covalently Closed Immune Modulating Oligodeoxyribonucleotides According to Claim 1 and Following Claims The synthesis of covalently closed immune modulating oligodeoxyribonucleotides was performed according to the teaching of EP 1 196 178 B1.

The ligation product was submitted to a final anion exchange chromatography in order to remove endotoxins (Carrier: LiChrospher DMAE, Merck Darmstadt, Germany; 0-1 M NaCl in 50 mM sodium phosphate) and concentrated by ethanol precipitation. The procedure was performed under sterile conditions for in-vivo experiments, and the final product is dissolved in sterile PBS.

EXAMPLE 2

Increased Cytokine Secretion Provoked by Immune Modulators on the Basis of DNA

Peripheral blood monocytes (PBMC) in RPMI 1640-medium were incubated in 96-well micro titer plates. The PBMC were stimulated by adding the following compounds: A: negative control, buffer, B: immune modulators on the basis of DNA C: linear, thioate-protected CpG oligonucleotides; and incubated for 48 h subsequently. Incubation was performed with equimolar amounts of the respective compounds (1 micromole/l). The supernatants of the incubations were removed and an ELISA assay was performed for the cytokines interferon gamma and interleukine-6. The results are given in FIG. 2. Delta Ct is given on the ordinate, delta Ct being the difference of the Ct values (reference minus cytokine)

EXAMPLE 3

Stimulation of Immunologically Relevant Surface Molecules on B Lymphocytes by Immune Modulators on the Basis of DNA An incubation of RPMI-8226 cells (a B-Lymphocyte cell line) was performed for 48 h with equimolar amounts of the respective compounds (1 micromole/l) (A: negative control, buffer, B: immune modulators on the basis of DNA C: linear, thioate-protected CpG oligonucleotides). Cells were harvested after the incubation, stained with fluorescently marked antibodies against the surface molecules HLA-DR and ICAM-1 and assayed by FACS. The ordinate of FIG. 3 shows fluorescence activity, the abscissa the cell size. Figure A shows the result of the assay of the buffer-stimulated B lymphocytes. According to this result, 9.7% of the viable cells are positive for the surface marker HLA-DR, 209.6% for ICAM-1. These values were taken as base level values. The results are represented in FIG. 3.

EXAMPLE 4

Increased Antibody Provoked by Immune Modulators on the Basis of DNA

Peripheral blood monocytes (PBMC) were incubated in 96-well microtitre plates in RPMI 1640 medium. The cells were stimulated by adding the following compounds: A: negative control, buffer, B: immune modulators on the basis of DNA C: linear, thioate-protected CpG oligonucleotides; and incubated for 48 h subsequently. Antibody titres for IgM, IgA and IgG were determined by ELISA. Antibody isotype titers for Ig1 and Ig2 were determined in order to arrive at a determination of the amount of humoral and cellular response, respectively. The measured titers can be taken as an indicator for the dominant subtype of the generated immune response. The results are represented in FIG. 4.

EXAMPLE 5

Comparison of Toxicity by Organ Enlargement

Female C57BL/6 mice were grouped into tree groups of 10 animals each. Animals were injected intraperitoneally with 100 microliters each of the following compounds: A: negative control, buffer; B: immune modulators on the basis of DNA; C: linear, thioate-protected CpG oligonucleotides. The concentration of the injected compounds was 2.5 microgram/ml and 60 microgram/ml. Animals were anesthesised and killed after one week. Spleen, liver, inguinal and mesenterial lymph nodes were isolated and their weight was determined. Statistical analysis was performed by ANOVA test. The results are given in FIG. 5 a, b, c.

EXAMPLE 6

Determination of Blood Clotting Time Influence

Peripheral blood monocytes (PBMC) were stimulated by adding the following compounds: A: negative control, buffer; B: immune modulators on the basis of DNA; C: linear, thioate-protected CpG oligonucleotides; and incubated for 3 minutes subsequently. After centrifugation, blood clotting time was determined as given by the parameter of partial thromboplastin time (aPPT) in seconds, as represented on the ordinate of FIG. 6. The values given there are derived from different blood donors. aPPT determination was performed according to BBL Fibro System Fibrometer (Becton Dickinson).

EXAMPLE 7

Determination of Recall Antigens after One Cycle of Chemotherapy

PBMC harvested after the first cycle of chemotherapy were analysed for the presence of recall-antigen-specific T lymphocytes. The determination of recall antigens was performed before and after therapy. The recall antigens determined were cytomegaly virus and Epstein-Barr virus (CMV, EBV). The determination was performed by fluorescence actived cell sorting (FACS) (see FIG. 7). Patient 12 showed an increase of CD8 positive cells of 723% after the first cycle.

EXAMPLE 8

Figure 8A:
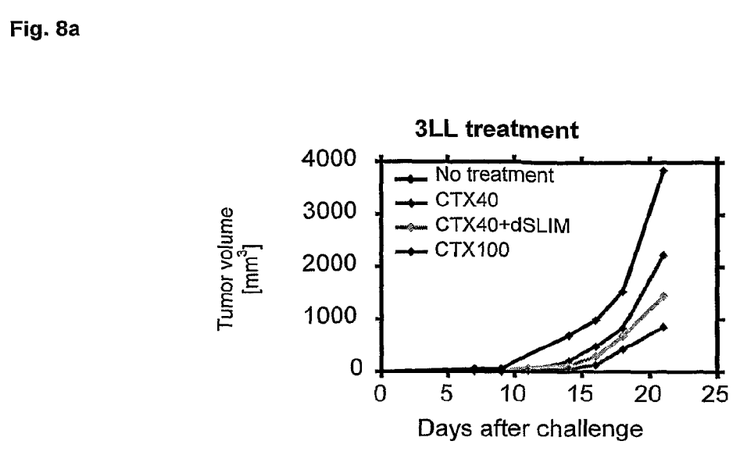
Figure 8B:
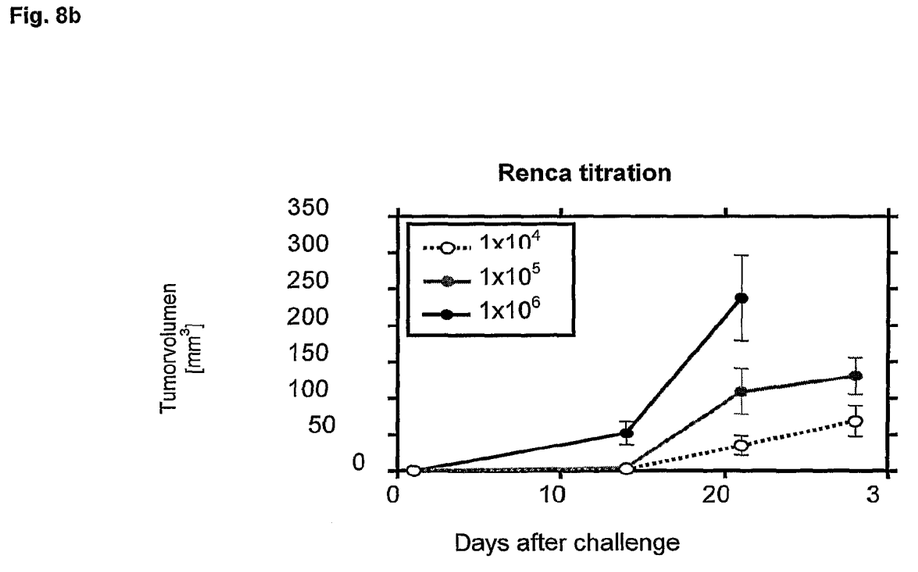

Evaluation of Anti-Tumor Effect of Immune Modulators on the Basis of DNA as Specified in the Present Invention in Animal Tumor Models An Evaluation of anti-tumor effect of immune modulators on the basis of DNA as specified in the present invention in animal tumor models was done in different models namely
a) Acute lymphocytic leukemia model (syngeneic): This determination was performed with murine BM185 cells, Balb/c mice. Immune modulators on the basis of DNA as specified in the present invention were combined with Imatinib.
b) Hepato cellular carcinoma model (syngeneic): This determination was performed with murine Hep22 cells, KM mice. Immune modulators on the basis of DNA as specified in the present invention were combined with 5-Fluorouracil (5-FU).
c) Lung cancer model (syngeneic): This determination was performed with murine 3LL cells, C57/BL6 mice. Immune modulators on the basis of DNA as specified in the present invention were combined with Paclitaxel, Cyclophosphamide, Gemcitabine and Cisplatin.
  The results are shown in FIG. 8a. Immune modulators on the basis of DNA as specified in the present invention are abbreviated as "dSLIM" according to a nomenclature of the applicant. It is obvious that a significant reduction of tumor volume is measured if—according to the present invention—a chemotherapeutic is given in combination with the immune modulator on the basis of DNA as specified in the present invention. Further, the drug amount of chemotherapeutics is significantly reduced compared with the drug amount without an immune modulator. Therefore, said combination is useful for any patient in favor to pre-vent the high drug amounts which are usually required to come to an equal result.
d) Renal cell carcinoma model (syngeneic): This determination was performed with murine Renca cells, Balb/c mice. Immune modulators on the basis of DNA as specified in the present invention were combined with 5-Fluorouracil (5-FU). The results are shown in FIG. 8b. It is obvious that—depending from the concentration—a significant reduction of tumor volume is measured. A reduction is shown in any case, independent from the concentration if—according to the present invention—a chemotherapeutic is given in combination with the immune modulator on the basis of DNA as specified in the present invention. Therefore, said combination is useful for any patient in favor to prevent the high drug amounts which are usually required to come to an equal result.
e) Melanoma model (syngeneic): This determination was performed with Murine B16 cells, CL57/BL6 mice. Immune modulators on the basis of DNA as specified in the present invention were combined with Dacarbacin (DTIC). Further studies in developing of animal models for preclinical efficacy studies confirm the above results, in particular

| | |
|---|---|
| Establishing non small cell lung cancer (NSCLC) animal model: Syngeneic murine 3LL model | 3LL titration finished Chemotherapy (CTX, Taxol, Gemcitabine, Cisplatin) evaluation |
| Establishing hepato cellular carcinoma (HCC) animal model: Syngeneic murine Hep22 model | Hep22 titration finished Chemotherapy (5-FU) evaluation |
| Establishing Melanoma animal model: Syngeneic murine B16 model | B16 titration finished Chemotherapy (DITC) evaluation |
| Establishing renal cellular carcinoma (RCC) animal model: Syngeneic murine Renca model | Renca titration finished Chemotherapy (5-FU) evaluation |
| Establishing colorectal carcinoma (CRC) animal model: Syngeneic murine C26 model | C26 titration finished |
| Establishing CRC animal model: Xenograph murine HT-29 model | HT-29 titration finished |
| Establishing Sarcoma animal model: Syngeneic murine S180 model | S180 titration finished Chemotherapy (CTX) evaluation |

Abbreviation:
CTX—Cyclophosphamid;
DITC—Dacarbacin;
5-FU—5-Fluorouracil

The invention claimed is:

1. A method for treating a human patient with a tumor comprising
  administering to said patient an immune modulator in an amount effective for generating a specific immune response against tumor antigens; and
  subsequently administering radiotherapy to said patient,
  wherein said tumor antigens are liberated by the radiotherapy, and
  wherein said immune modulator comprises a circular single strand of deoxyribonucleic acid of 40 to 200 nucleotides with a partially complementary antiparallel base sequence, said partial complementarity providing a dumbbell-shaped molecule, and
  wherein said immune modulator comprises the sequence $N^1N^2CGN^3N^4$ within both of the loop portions of the dumbbell-shaped molecule, wherein $N^1N^2$ is GT, GG, GA, AT or AA and $N^3N^4$ is CT or TT, and wherein C is deoxycytosine, G is deoxyguanosine, A is deoxyadenosine and T is deoxythymidine.

2. A method for treating a human patient with a tumor comprising
  administering to said patient an immune modulator in an amount effective for generating a specific immune response against tumor antigens; and
  subsequently administering chemotherapy to said patient,
  wherein said tumor antigens are liberated by the chemotherapy, and
  wherein said immune modulator comprises a circular single strand of deoxyribonucleic acid of 40 to 200 nucleotides having a partially complementary antiparallel base sequence, said partial complementarity providing a dumbbell-shaped molecule, and
  wherein said immune modulator comprises the sequence $N^1N^2CGN^3N^4$ within both of the loop portions of the dumbbell-shaped molecule, wherein $N^1N^2$ is GT, GG, GA, AT or AA and $N^3N^4$ is CT or TT, and wherein C is deoxycytosine, G is deoxyguanosine, A is deoxyadenosine and T is deoxythymidine.

3. The method of claim 2 further comprising administering the immune modulator after the chemotherapy.

4. The method of claim 2 wherein the chemotherapy comprises treatment with a topoisomerase inhibitor, an alkylating agent, a platin compound, an antimetabolite, an anthracycline, an actinomycin, a vinca alkaloid, a taxane, an antiestrogen or combinations thereof.

5. The method of claim 1 or 2 wherein the immune modulator is administered intradermally, subcutaneously or intramuscularly.

6. The method of claim 1 or 2 wherein the immune modulator is administered as two injections of 0.5 mg on the same day, and the administration is repeated at intervals between two and eight days.

7. The method of claim 1 wherein said patient receives a cumulative total of 1 mg to 10 mg of the immune modulator prior to receiving radiotherapy.

8. The method of claim 2 wherein said patient receives a cumulative total of 1 mg to 10 mg of the immune modulator prior to receiving chemotherapy.

* * * * *